United States Patent [19]
Dinsmore

[11] Patent Number: 4,635,296
[45] Date of Patent: Jan. 6, 1987

[54] WIDE BANDWIDTH ULTRA HIGH STABILITY FM TELEMETRY TRANSMITTER

[75] Inventor: Mark T. Dinsmore, Newton, Mass.

[73] Assignee: Transkinetic Systems, Inc., Canton, Mass.

[21] Appl. No.: 704,654

[22] Filed: Feb. 22, 1985

[51] Int. Cl.[4] .............................................. H04B 1/04
[52] U.S. Cl. ...................................... 455/113; 455/119; 455/127; 340/870.37; 340/870.39; 331/177 V; 332/30 V
[58] Field of Search ............... 455/110, 113, 119, 126, 455/117, 127, 300; 332/30 V; 340/663, 870.26, 870.37, 870.39, 870.28; 331/67, 70, 186, 177 V

[56] References Cited
U.S. PATENT DOCUMENTS

| | | | |
|---|---|---|---|
| 3,204,201 | 8/1965 | Bahrs | 331/67 |
| 3,697,886 | 10/1972 | Conn et al. | 455/127 |
| 3,832,629 | 8/1974 | Cernek, Jr. | 340/663 |
| 3,979,657 | 9/1976 | Yorksie | 340/663 |
| 4,375,621 | 3/1983 | Schneiter et al. | 332/30 V |

Primary Examiner—Jin F. Ng
Attorney, Agent, or Firm—Weingarten, Schurgin, Gagnebin & Hayes

[57] ABSTRACT

An FM transmitter especially for physiological signal telemetry includes a transistor oscillator having a collector-to-base capacitance that is part of its tuned circuit. Means are disclosed for controllably varying the collector-to-base capacitance only in response to impressed physiological or other signals to provide FM modulated signals for aerial transmission to any suitable receiver. Means including cooperative constant emitter current and constant collector voltage DC biasing circuits are disclosed for eliminating undesirable, changing temperature induced frequency variations. Means are further disclosed for neutralizing undesirable antenna loading induced frequency variations. The system is capable of accepting multiplexed inputs.

20 Claims, 2 Drawing Figures

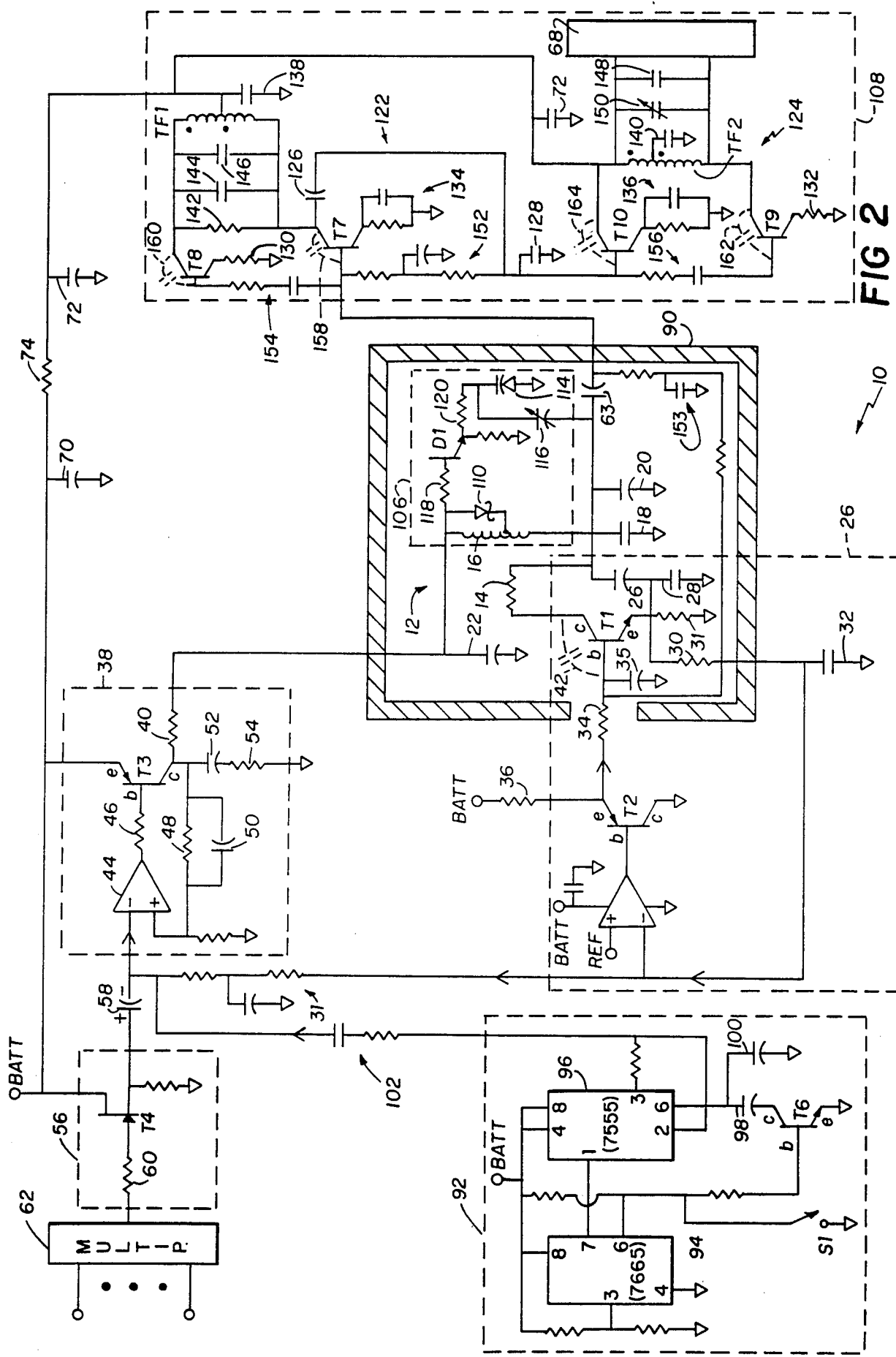

WIDE BANDWIDTH ULTRA HIGH STABILITY FM TELEMETRY TRANSMITTER

FIELD OF THE INVENTION

This invention is directed to the field of radio communications, and more particularly, to a novel wide bandwidth high stability FM telemetry transmitter.

BACKGROUND OF THE INVENTION

Wireless telemetry of phsiological signals is desirable for sports medicine, cardiac rehabilitation, and critical care monitoring, among other applications. Wireless telemetry of the electrocardiographic activity of ambulatory patients, for example, makes possible the aquisition of data representative of the degree of cardiac dysfunction while a patient is in movement and therewith provides an increased diagnostics capability and better patient care. In sports medicine applications, wireless telemetry of electrocardiographic and electromuscular signals provides data representative of the physiological conditions of strenuously exercising patients. In critical care units, wireless telemetry of the physiological conditions of critically ill patients reduces patient clutter and substantially eliminates the troublesome wire leads and connections that characterize conventional critical care monitoring units. Wireless telemetry of the physiological condition of non-human subjects such as laboratory test animals is also desirable in many situations.

Wireless telemetry systems for monitoring the physiological conditions of human and non-human subjects must provide a signal that is invariant with respect to temperature conditions, placement conditions, and other application environment variables so that reliable and repeatable data transmission is ensured. The transmitted data moreover must be as clean and noise-free as possible to provide such a high confidence level that accurate patient diagnosis therefrom can be accomplished. Such systems should additionally be capable of telemetering several signals from a subject simultaneously to provide a monitoring capability of one or more physiological conditions from one or more bodily locations. At the same time, such systems are called upon to be of comparatively light-weight and of a small size so as to enable ease of patient placement and comfortable non-obtrusive usage.

SUMMARY OF THE INVENTION

The wide bandwidth high stability FM transmitter of the present invention provides highly reliable and repeatable signal telemetry that is free from undesirable thermal and loading effects while utilizing a minimum number of components that makes it compact and light-weight enough for physiological telemetry. The FM transmitter of the present invention includes a variable frequency oscillator having a wide bandwidth tuneable circuit, contemplates means coupled to the variable frequency oscillator for completely stabilizing it against changing temperature induced frequency variations, and further contemplates means coupled to the oscillator for neutralizing loading induced frequency variations.

The FM transmitter of the present invention includes a transistor oscillator and a wide bandwidth LC tuned circuit in a Colpitts configuration. A combination negative feedback circuit for maintaining a constant biasing transistor emitter current and a voltage regulator for maintaining a constant D.C. bias collector voltage are provided for completely stabilizing the transistor oscillator against changing temperature induced frequency variations. A clamping and modulation circuit including a schottky diode across a portion of the LC tuned circuit is provided in one embodiment for maintaining radio frequency oscillation within the linear region of the transistor oscillator. The temperature stabilized variable frequency transistor oscillator and wide bandwidth LC tuned circuit of the present invention are coupled to an output stage having a power amplifier and an antenna, and in one embodiment a phase inverting feedback transformer buffer having a manually adjustable capacitor is provided between the oscillator and output stage for neutralizing loading induced frequency variations. In another embodiment, a two stage buffer and amplifier is provided therebetween with each stage having matched transistors and a self neutralizing push/pull transformer arrangement. Radio frequency shielding is provided at least around the variable frequency oscillator in both embodiments for further neutralizing loading effects. Signal potentials representative of physiological conditions are applied to the collector of the transistor and modulate the LC tuned circuit by varying the collector to base capacitance. A multiplexer is provided for telemetry of multiple inputs simultaneously. The tuned circuit components are preferably high quality and include a monolithic thin-film ceramic inductor. Means are provided for producing an alarm signal and an automatic transmitter shut off for low-battery voltage conditions especially useful for in-patient hospital care.

BRIEF DESCRIPTION OF THE DRAWINGS

These and other features and advantages of the present invention will become apparent as the invention becomes better understood by referring to the following solely exemplary and non-limiting detailed description of the invention, and to the drawings, wherein:

FIG. 2 is a schematic diagram of another embodiment of the wide bandwidth ultra stable FM transmitter according to the present invention.

DETAILED DESCRIPTION OF THE PREFERRED EMBODIMENTS

Figure 1:
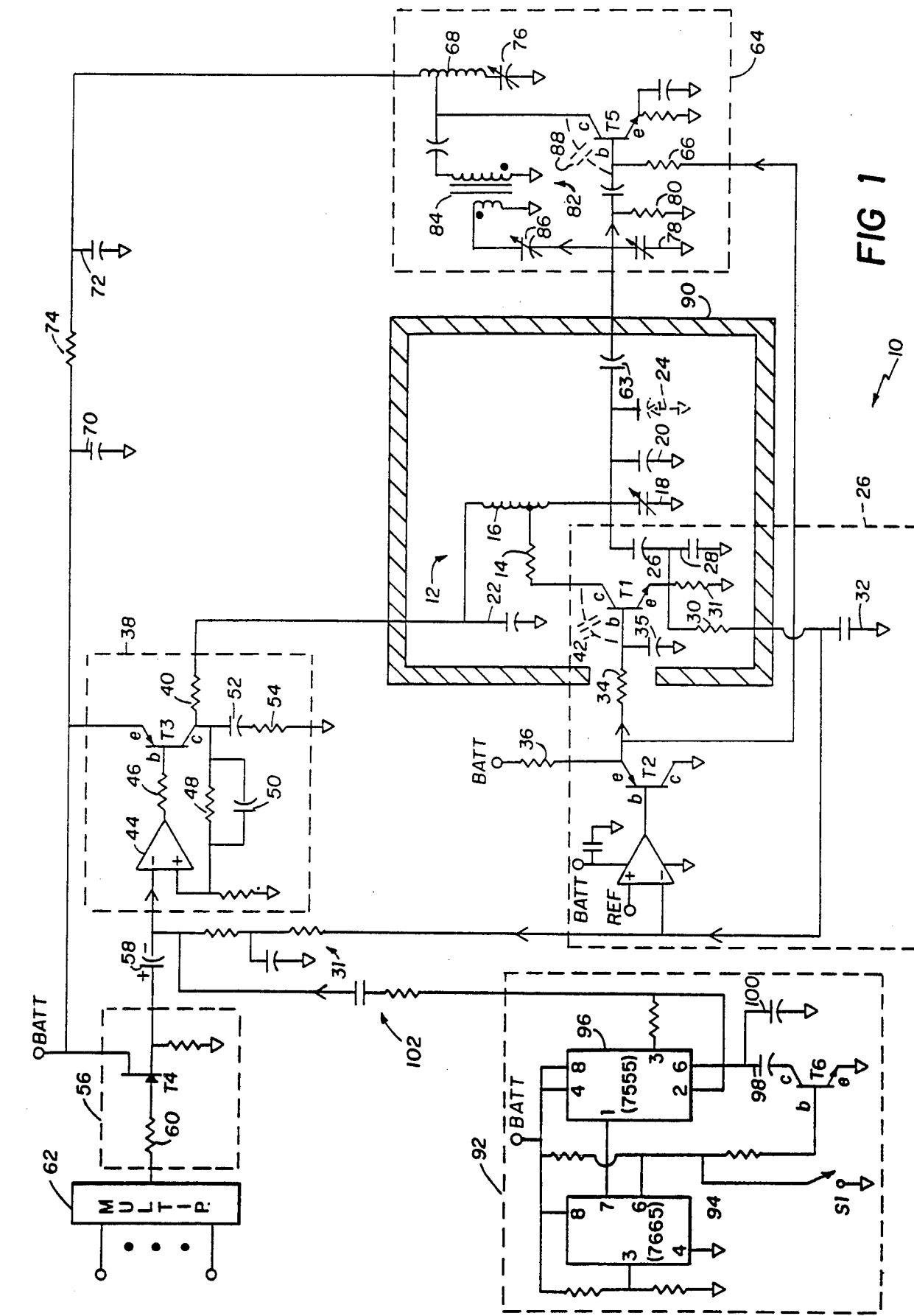
FIG. 1 is a schematic diagram of one embodiment of the wide bandwidth ultra stable FM transmitter according to the present invention.

Referring now to FIG. 1 of the drawings, generally designated at 10 is a schematic circuit diagram of one embodiment of the novel wide bandwidth, ultrastable FM transmitter according to the present invention. The transmitter 10 includes a variable frequency transistor oscillator generally designated 12. The oscillator 12 includes a transistor T1 having a collector designated "c", an emitter "e", and a base designated "b". The collector of the transistor T1 is connected via a resistor 14 to an inductor 16. The inductor 16 is preferably a high quality monolithic thin-film ceramic inductor having a very low coefficient of thermal stability (ppm/°C.). The inductor 16 is preferably center-tapped. A variable capacitor 18 in parallel with a fixed capacitor 20 is connected between one end of the inductor 16 and circuit ground. A high frequency grounding capacitor 22 is connected to the other end of the inductor 16. The high-frequency grounding capacitor 22 effectively connects the inductor 16 in parallel with the capacitors 18, 20 providing a High Q, wide tuning bandwidth resonant tank circuit. A varactor illustrated dashed at 24 may be provided in parallel with the capacitors 18, 20 to provide for scale change of the modulation index. A capacitor divider including capacitors 26, 28 is connected in series between the tank and ground, and the emitter of the transistor T1 is connected at the mid-point of the capacitor divider to provide regenerative feedback. A resistor 31 is connected in parallel across the capacitor 28. It will be appreciated that the just described variable frequency transistor oscillator having a wide bandwidth tuned circuit is arranged in a so-called Colpitts configuration. The elements 16, 18, 20, 22, and 26 are preferably very high quality components selected to exhibit a high frequency stability. A stability of 30–40 ppm/°C. or less is desirable.

A feedback loop illustrated by a dashed box 26 is coupled to the oscillator 12 for maintaining the transistor T1 emitter current constant. The constant emitter current holds the collector current constant against temperature induced variations, which would otherwise change the transistor transition frequency f' and therewith the oscillation frequency. The negative feedback loop 26 includes an operational amplifier (op amp) 28. The inverting input of the amplifier 28 is connected via a resistor 30 to the emitter of the transistor T1 of the variable frequency transistor oscillator 12, and the non-inverting input thereof is connected to a preselected reference voltage designated "REF". The inverting input is also connected to the non-inverting input of an op amp 44 to be described via a filter generally designated 33 for applying a very stable reference voltage thereto. The resistor 30 and a capacitor 32 provide a filter in the negative feedback loop. The output of the op amp 28 is connected through an emitter follower transistor T2 to the base of the transistor T1 of the oscillator 12 via a resistor 34 and grounded capacitor 35. The resistor 34 and capacitor 35 provide an oscillation frequency ground. The emitter follower transistor T2 preferably has a wide bandwidth and a unity gain. The transistor T2 is biased via a resistor 36 connected to a controlled source of constant potential designated "trans enable", to be described. The op amp 28 is operative in response to deviations either above or below its set point to produce a corrective signal that cancels the deviations and maintains the emitter biasing current constant through the transistor T1 of the oscillator 12. The op amp 28 thereby also provides the very stable reference voltage to the op amp 44.

A voltage regulator and amplifier illustrated in dashed line 38 is coupled to the collector of the transistor T1 of the oscillator 12 via a resistor 40 and the top of the inductor 16. The voltage regulator and amplifier 38 is operative to maintain the voltage on the collector of the transistor T1 constant at a preselected value which further regulates the collector-to-base capacitance, as illustrated in dashed line 42, to stabilize the oscillator 12 against changing temperature induced frequency drifting. If the base voltage is changing, for example, by approximately $-2.2$ mv/°C. to keep the emitter voltage and current constant, the voltage from the collector to emitter is changing by approximately $+2.2$ mv/°C. The temperature dependent term of the collector to base capacitance is thereby cancelled, according to the relation:

$$C_{cb} = C_d/(V+\phi)^{0.5} + C \text{ stray}$$

where $C_d$ is the capacitance of the collector to base diode, which is a constant; V is the voltage applied to the collector to base, which is some constant plus 2.2 mv/°C.; and where $\phi$ is the contact potential, which is some constant minus 2.2 mv/°C. Since "$V+\phi$" equals a "constant $+2.2$ mv/°C.+constant $-2.2$ mv/°C.", it will be appreciated that the positive and negative terms cancel and $C_{cb}$ is a constant with temperature. The voltage regulator and amplifier 38 includes an op amp 44 the output of which is connected via a resistor 46 to the base of a grounded emitter amplifing transistor T3. The collector of the transistor T3 is connected via a feedback network including a parallel resistor 48 and a capacitor 50 to the non-inverting input of the op amp 44. The emitter of the transistor T3 is connected to the source of applied potential designated "BATT". The transistor T3 produces an inverted output which, when applied through the feedback network to the op amp 44, maintains the output of the transistor constant against fluctuation so as to maintain a constant voltage on the collector of the transistor T1 of the variable frequency oscillator 12.

A high input impedance buffer illustrated in dashed line 56 is connected to the inverting input of the op amp 44 of the voltage regulator and amplifier 38 via a coupling capacitor 58. The high input impedance buffer 56 includes an FET T4 connected between the battery and the ground and connected via a resistor 60 to a multiplexer 62. Input physiological signals impressed on the inputs to the multiplexer 62 are serially coupled through the high input impedance buffer 56, which matches the transmitter impedance to the typically high impedance of the signal inputs. The voltage regulator and amplifier 38 is responsive to the serially applied signal inputs and is operative to provide an amplified input signal. The amplified input signal is applied to the oscillator 12 and acts to change the voltage on the transistor T1. The effect is to vary the collector-to-base capacitance 42 in a precisely controlled manner. The variations in the collector-to-base capacitance alter the frequency of the tuned circuit including the elements 16, 18, 20 of the oscillator 12 providing very reliable and highly repeatable FM modulation in a manner completely free from both undesirable time and temperature change induced frequency deviations.

The ultra stable frequency modulated signal is coupled via a coupling capacitor 63 to an output stage illustrated by a dashed box 64 for amplification and radiation to an associated telemetry receiver, not shown. The output stage 64 includes a transistor T5 that enhances the power of the frequency modulated signal. The transistor T5 is preferably the same as the transistor T1, and is preferably biased the same via a resistor 66 connected to the output of the transistor T2 in the negative feedback constant biasing current stabilization loop 26. The bias on the transistor T5 is thus provided without requiring a separate voltage divider network, which helps to keep components and current consumption to a minimum. The collector of the transistor T5 is connected to an antenna 68. The antenna 68 preferably is a loop antenna. One end of the antenna 68 is connected to the battery via an AC ground consisting of capacitors 70, 72 and a resistor 74, and the other end of the antenna 68 is connected to ground via a variable capacitor 76. A parallel variable capacitor 78 and resistor 80 arrangement is provided between the output of the variable frequency oscillator 12 and the output of the output stage 64 to provide impedance matching to optimize power coupled from the oscillator to the output stage on the one hand and isolation between the oscillator and output stage on the other.

A neutralizing circuit generally designated 82 is provided in a feedback path between the collector of the transistor T5 and the base thereof. The neutralizing circuit 82 preferably includes a phase inverting feedback transformer buffer 84 and a variable capacitor 86. Loading at the antenna 68 caused by its proximity to physical objects in its near field couples back through the collector-to-base capacitance of the transistor T5 illustrated dashed at 88 and is neutralized by the phase inverting buffer which induces an equal but opposite magnitude signal that cancels the loading feedback. To initially set up the neutralizing circuit, it should be noted that all that is necessary is to move ones hand close to the antenna 68 and simultaneously adjust the variable capacitor 86 until the motion of the hand produces no result. A shield illustrated in hatched outline 90 is provided around the variable frequency oscillator 12 to further prevent undesirable loading induced frequency changes on the oscillator.

A battery voltage sensing circuit illustrated by a dashed box 92 is coupled to the battery for providing a signal indication of low battery and automatic shut off for a failed battery condition. The circuit 92 includes a dual comparator with a dual threshold 94 operatively connected to an astable multivibrator 96. The comparator 94 preferably is an Intersil chip number 7665, and the astable multivibrator 96 preferably is an Intersil chip number 7555. A normally on switching transistor T6 is connected via parallel capacitors 98, 100 to the frequency determining inputs of the astable multivibrator 96. A nurse call switch S1 is connected across the base to emitter terminals of the switching transistor T6. So long as the battery voltage applied to the reference input pin designated "6" does not fall below a first predetermined value, the output of the comparator 94 on the pin designated "7" is high, and the astable multivibrator is disabled. Whenever the battery level drops below the first preselected threshold level, the output of the comparator 94 goes low, and enables the astable multivibrator 96 at a preselected first frequency determined by the parallel combination of the capacitors 98, 100. A resistor 101 connected between the battery and the ground pin of the astable multivibrator 96 draws sufficient current when the comparator 94 is enabled so that the battery voltage cannot recover when the oscillator current is shut off. Whenever a nurse call is requested, by closing the switch S1, it turns the switching transistor T6 "off", and therewith so changes the capacitance to the frequency determining pins 2, 6 of the multivibrator 96 that it produces a second predetermined frequency indicative of the nurse call request. The output signals are applied via a filter generally designated 102 to the inverting input of the op amp 44 for eventual transmission to the remote receiver over the antenna 68. Whenever the voltage at the pin 3 of the comparator 94 falls below a second preselected voltage, the voltage designated "trans enable" to the oscillator bias resistor 36 is removed, and the RF oscillator 12 is therewith disabled. This prevents circuit deregulation and drifting in frequency to another, undesired channel. A resistor 103 connected at the pin 3 of the comparator 94 provides a hysteresis function during oscillator shutoff which prevents switching the oscillator "on" and "off" rapidly as the shutoff threshold is crossed.

Referring now to FIG. 2, generally designated at 104 is another embodiment of the wide bandwidth ultra high stability FM telemetry transmitter according to the present invention. Similar elements between the embodiments of FIGS. 1 and 2 are identically designated and are not further discussed for brevity of explication. The embodiment of FIG. 2 primarily differs from that of FIG. 1 by its inclusion of a clamping mechanism illustrated by a dashed box 106 to be described and by its provision of a two-stage neutralizing and amplifying circuit coupled between the output of the RF oscillator and the antenna illustrated by a dashed box 108 to be described.

The clamping and modulation circuit 106 includes a schottky diode 110 in parallel with a portion of the inductor 16, which is connected to the collector of the transistor T1 via the resistor 14, unlike in the embodiment of FIG. 1 where the inductor was tapped and returned to the collector of the transistor 16. The diode 110 limits the voltage at the collector of the transistor T1 enough to linearize the operation of the transistor to eliminate undesirable temperature effects. In this way, the transistor oscillator has been found to have a stability on the order of 20 ppm/°C. A varactor 114 connected to an adjustable capacitor 116 is connected to the clamped inductor via series resistors 118, 120 and a transistor D1 that is operated as a diode. The transistor D1 has a temperature coefficient that is selected to compensate for temperature drift of the varactor 114. The varactor 114 and adjustable capacitor 116 are operative to provide a selectable modulation index.

The two-stage neutralized buffer and amplifier 108 includes a first stage generally designated 122 connected to the output of the transistor oscillator 12 and a second stage generally designated 124 connected via a coupling capacitor 126 between the output of the stage 122 and the loop antenna 68. A capacitor 128 in conjunction with the capacitor 126 provides impedance matching between the stages to provide appropriate power transfer and stage isolation.

The stage 122 and the stage 124 each include dual transistors T7, T8 and T9, T10 whose collectors are respectively electrically connected to phase inverted terminals of push/pull transformers TF1, TF2. The transformers TF1, TF2 are each so designed that their two winding halves are very tightly coupled at their operating frequency and thus produce precisely opposite voltages at the transformer output terminals. The emitters of the transistors T8, T9 are connected to circuit ground via resistors 130, 132, and the emitters of the transistors T7, T10 are connected to circuit ground by parallel RC networks generally designated 134, 136. The transformer TF1 preferably is a bifilar wound high frequency toroid having a comparatively low inductance, and the transformer TF2 preferably is a bifilar wound powdered metal toroid with a comparatively higher inductance. The transformers TF1 and TF2 are respectively center-tapped to circuit ground via capacitors 138, 140.

A parallel arrangement of a resistor 142, a capacitor 144, and a variable capacitor 146 is provided across the terminals of the transformer TF1, and a parallel arrangement of a capacitor 148 and variable capacitor 150 is provided across the terminals of the transformer TF2. The elements 142, 144, 146, 148, and 150 provide a Q and frequency selectable resonance characteristic. A biasing resistor/capacitor arrangement generally designated 152 is connected between the output of the oscillator and transistor T7 to the base of the transistor T10 and a biasing resistor/capacitor arrangement generally designated 153 is connected between the bases of the transistor T1 and the base of the transistor T7. A series RC coupling circuit generally designated 154 is connected between the bases of the transistors T7, T8, and a series RC coupling circuit generally designated 156 is connected between the bases of the transistors T9, T10. Each of the transistors T7, T8, T9, and T10 have a corresponding collector-to-to base capacitance schematically illustrated in dashed outline 158, 160, 162, and 164.

In operation, the two-stage neutralized buffer and amplifier 108 amplifies the frequency modulated telemetry signal produced by the transistor oscillator 12 and feeds it forward to the loop antenna 68 for radiation and eventual reception by an associated telemetry receiver while providing isolation backwards from the loop antenna 68 for loading induced frequency variations. Any loading at the antenna 68 caused by its proximity to physical objects in its near field couples back through the collector-to-base capacitances 158, 160, 162 and 164 of the transistors T7, T8, T9, and T10. Since the voltage at the phase inverted terminals of the push/pull transformers TF1, TF2 are equal and opposite, the current through the collector-to-base capacitors 158, 160 of the stage 122 as well as the currents through the collector-to-base capacitances 162, 164 of the stage 124 are equal and opposite. The equal and opposite currents cancel each other and thereby neutralize any undesirable loading feedback.

The stage 124 of the two-stage neutralizing buffer and amplifier 108 is further operative to proportionately decrease the magnitude of reflected loading induced effects when the antenna is asymmetrically loaded, and completely eliminates loading when the antenna is symmetrically loaded. Each half of the loop antenna 68 is connected to a corresponding one of the transistors T9, T10 such that, a hand, for example, approaching the antenna 68 asymmetrically from either above or below the loop would appear only across one half of the stage 124 so that the effective capacitance reflected back to the input would be reduced by a factor of one fourth. If the loop antenna is symmetrically loaded, the currents through the collector-to-base capacitances 102, 104 of the transistors T9, T10 in being equal and opposite cancel, and in such a way that the reflected capacitance is thereby reduced to zero. Each half of the loop antenna is isolated from the other half. The couling transformer TF2 forces the voltage at its terminals to have an equal magnitude but an opposite sign. Preferably, the inductance of the transformer TF2 is selected to be about 5 to 10 times that of the loop antenna 68.

It will be appreciated that many modifications of the presently disclosed invention will become apparent to those skilled in the art without departing from the scope of the appended claims.

What is claimed is:

1. An ultra stable wide bandwidth transmitter for providing frequency modulation of predetermined input signals, comprising:
   a variable frequency oscillator including a wide bandwidth tuneable circuit, a transistor having a base, a collector, an emitter, and a collector-to-base capacitance, and a regenerative feedback loop connected between said tuneable circuit and said transistor in such a way that said collector-to-base capacitance is an operative part of said wide bandwidth tuneable circuit;
   means coupled to said variable frequency oscillator for establishing and maintaining a preselected constant emitter biasing current through said transistor for regulating and stabilizing the collector current of said transistor against changing temperature induced variations;
   said constant emitter biasing current establishing and maintaining means includes a voltage reference, and a negative feedback loop connected between said voltage reference and said emitter of said transistor for driving said base of said transistor of said variable frequency oscillator for maintaining said constant emitter current;
   means coupled to said variable frequency oscillator for establishing and maintaining a constant biasing voltage at said collector of said transistor of said variable frequency oscillator for regulating and stabilizing said collector-to-base capacitance against changing temperature induced variations;
   means coupled to said variable frequency oscillator for controllably varying said collector-to-base capacitance and therewith the frequency of said tuned circuit in response to said input signals to provide frequency modulated signals representative thereof;
   an output stage coupled to said variable frequency oscillator including an antenna; and
   means coupled between said output stage and said variable frequency oscillator for compensating and neutralizing antenna loading induced frequency variations.

2. The invention of claim 1, wherein said wide bandwidth tuneable circuit includes an inductor and a capacitor in parallel.

3. The invention of claim 2, wherein said inductor of said tuned circuit consists of a thin-film monolithic ceramic inductor.

4. The invention of claim 1, wherein said variable frequency oscillator including said wide bandwidth tuneable circuit and said transistor are operatively connected in said regenerative feedback loop in a Colpitts configuration.

5. The invention of claim 1, further including a shield disposed surrounding said variable frequency oscillator for further neutralizing antenna induced loading frequency variations.

6. The invention of claim 1 wherein said negative feedback loop includes an operational amplifier operatively connected to an emitter follower transistor stage, and further includes a high frequency oscillator ground connected between said emitter follower transistor stage and said base of said transistor.

7. The invention of claim 1, wherein said constant collector biasing voltage establishing and maintaining means includes a voltage regulator.

8. The invention of claim 7, wherein said voltage regulator includes an operational amplifier, and a grounded emitter follower transistor stage operatively connected in a second negative feedback loop therewith.

9. The invention of claim 7, wherein said voltage regulator is operatively connected to said collector of said transistor of said variable frequency oscillator, and wherein said collector-to-base capacitance varying means includes a high impedance input buffer connected to said voltage regulator having an input responsive to said input signals.

10. The invention of claim 9, further including a multiplexer connected to said high input impedance buffer between said input and said inputs.

11. The invention of claim 1, wherein said output stage further includes a transistor amplifier operatively connected to said antenna and responsive to said frequency modulated signal.

12. The invention of claim 11, wherein said loading compensating and neutralizing means includes a phase inverting transformer buffer operatively coupled to said antenna, said output stage transistor, and to said frequency modulated signal.

13. The invention of claim 1, further including a battery having a voltage for powering said transistor of said variable frequency oscillator, and further including means connected to said oscillator and responsive to said battery voltage for providing an alarm condition signal whenever said battery voltage falls to below a predetermined first level, and for shutting down said variable frequency oscillator whenever said battery voltage falls below a second predetermined level lower than said first predetermined level.

14. An ultra stable wide bandwidth transmitter for providing frequency modulation of predetermined input signals, comprising:
a variable frequency oscillator including a wide bandwidth tuneable circuit, a transistor having a base, a collector, an emitter, a linear amplitude range and a collector-to-base capacitance, and a regenerative feedback loop connected between said tuneable circuit and said transistor in such a way that said collector-to-base capacitance is an operative part of said wide bandwidth tuneable circuit;
means coupled to said tuneable circuit for limiting amplitude oscillation of said variable frequency oscillator to within the linear amplitude range of said transistor without changing the operative frequency of oscillation;
means coupled to said variable frequency oscillator for establishing and maintaining a preselected constant emitter biasing current through said transistor for regulating and stabilizing said collector current of said transistor against changing temperature induced variations;
means coupled to said variable frequency oscillator for establishing and maintaining a constant biasing voltage at said collector of said transistor of said variable frequency oscillator for regulating and stabilizing said collector-to-base capacitance against changing temperature induced variations;
means coupled to said variable frequency oscillator for controllably varying said collector-to-base capacitance and therewith the frequency of said tuned circuit in response to said input signals to provide frequency modulated signals representative thereof;
an output stage coupled to said variable frequency oscillator including an antenna; and
means coupled between said output stage and said variable frequency oscillator for compensating and neutralizing antenna loading induced frequency variations.

15. An ultra stable wide bandwidth transmitter for providing frequency modulation of predetermined input signals, comprising:
a variable frequency oscillator including a wide bandwidth tuneable circuit, a transistor having a base, a collector, an emitter, and a collector-to-base capacitance, and a regenerative feedback loop connected between said tuneable circuit and said transistor in such a way that said collector-to-base capacitance is an operative part of said wide bandwidth tuneable circuit;
means coupled to said variable frequency oscillator for establishing and maintaining a preselected constant emitter biasing current through said transistor for regulating and stabilizing the collector current of said transistor against changing temperature induced variations;
means coupled to said variable frequency oscillator for establishing and maintaining a constant biasing voltage at said collector of said transistor of said variable frequency oscillator for regulating and stabilizing said collector-to-base capacitance against changing temperature induced variations;
means coupled to said variable frequency oscillator for controllably varying said collector-to-base capacitance and therewith the frequency of said tuned circuit in response to said input signals to provide frequency modulated signals representative thereof;
an output stage coupled to said variable frequency oscillator including an antenna;
means coupled between said output stage and said variable frequency oscillator for compensating and neutralizing antenna loading induced frequency variations;
said compensating and neutralizing means includes a two-stage neutralizing buffer and amplifier arrangement operative to feed power forward fromt he variable frequency oscillator to said antenna and operative to isolate loading feedback backward from said antenna to said variable frequency oscillator;
one of said stages includes two closely matched and identical transistors each having a collector, and further includes a push/pull transformer having phase inverted terminals operatively connected to corresponding ones of said collectors of said closely matched and identical transistors such that antenna loading produces cancelling currents through corresponding ones of said transistors thereby neutralizing said loading.

16. The invention of claim 15 wherein the other one of said stages includes two closely matched and identical transistors each having a collector, and further includes a push/pull transformer having phase inverted terminals operatively connected to corresponding ones of said collectors of said closely matched and identical transistors such that antenna loading produces canceling currents through corresponding ones of said transistors thereby neutralizing said loading.

17. An ultra stable wide bandwidth transmitter for providing frequency modulation of predetermined input signals, comprising:
a variable frequency oscillator including a wide bandwidth tuneable circuit, a transistor having a base, a collector, an emitter, and a collector-to-base capacitance, and a regenerative feedback loop connected between said tuneable circuit and said transistor in such a way that said collector-to-base capacitance is an operative part of said wide bandwidth tuneable circuit;

means coupled to said variable frequency oscillator for establishing and maintaining a preselected constant emitter biasing current through said transistor for regulating and stabilizing the collector current of said transistor against changing temperature induced variations;

means coupled to said variable frequency oscillator for establishing and maintaining a constant biasing voltage at said collector of said transistor of said variable frequency oscillator for regulating and stabilizing said collector-to-base capacitance against changing temperature induced variations;

means coupled to said variable frequency oscillator for controllably varying said collector-to-base capacitance and therewith the frequency of said tuned circuit in response to said input signals to provide frequency modulated signals representative thereof;

an output stage coupled to said variable frequency oscillator including an antenna, and a transistor amplifier operatively connected to said antenna; and means coupled between said output stage and said variable frequency oscillator for compensating and neutralizing antenna loading induced frequency variations, said loading and compensating means including a phase inverting transformer buffer operatively coupled to said antenna, said output stage transistor and to receive said frequency modulated signal.

18. An ultra stable wide bandwidth transmitter for providing frequency modulation of predetermined input signals, comprising:

a variable frequency oscillator including a wide bandwidth tuneable circuit, a transistor having a base, a collector, an emitter, a collector-to-base capacitance, and a linear range, and a regenerative feedback loop connected between said tuneable circuit and said transistor in such a way that said collector-to-base capacitance is an operative part of said wide bandwidth tuneable circuit;

said tuneable circuit including a capacitor and an inductor;

means coupled to said tuneable circuit for limiting oscillation of said variable frequency oscillator to within the linear range of said transistor, said oscillation limiting means includes a shottky diode clamped across said inductor;

means coupled to said variable frequency oscillator for establishing and maintaining a preselected emitter biasing current through said transistor for regulating and stabilizing the collector current of said trnsistor against changing temperature induced variations;

means coupled to said variable frequency oscillator for establishing and maintaining a constant biasing voltage at said collector of said transistor of said variable frequency oscillator for regulating and stabilizing said collector-to-base capacitance against changing temperature induced variations;

means coupled to said variable frequency oscillator for controllably varying said collector-to-base capacitance and therewith the frequency of said tuneable circuit in response to said input signals to provide frequency modulated signals representative thereof;

an output stage coupled to said variable frequency oscillator including an antenna for radiating said frequency modulated signals; and means coupled between said output stage and said variable frequency oscillator for compensating and neutralizing antenna loading induced frequency variations.

19. The invention of claim 18, further including means coupled to said clamped inductor for providing a selectable modulation index.

20. The invention of claim 19, wherein said selectable modulation index providing means includes a varactor.

* * * * *

UNITED STATES PATENT AND TRADEMARK OFFICE
CERTIFICATE OF CORRECTION

PATENT NO. : 4,635,296

DATED : January 6, 1987

INVENTOR(S) : Mark T. Dinsmore

It is certified that error appears in the above-identified patent and that said Letters Patent is hereby corrected as shown below:

Column 3, line 22, "frequency f" should read --frequency ft--.

Column 4, line 67, "output of the output" should read --input of the output--.

Signed and Sealed this

Thirty-first Day of July, 1990

*Attest:*

*Attesting Officer*

HARRY F. MANBECK, JR.

*Commissioner of Patents and Trademarks*